United States Patent
Zhang et al.

(10) Patent No.: US 8,829,226 B2
(45) Date of Patent: Sep. 9, 2014

(54) LACOSAMIDE INTERMEDIATE COMPOUND, PREPARATION METHOD THEREOF AND USE THEREOF

(75) Inventors: Xianyi Zhang, Zhejiang (CN); Shaoqing Ge, Zhejiang (CN); Daqing Che, Brantford (CA)

(73) Assignee: Zhejiang Jiuzhou Pharmaceutical Co., Ltd, Taizhou (CN)

( * ) Notice: Subject to any disclaimer, the term of this patent is extended or adjusted under 35 U.S.C. 154(b) by 164 days.

(21) Appl. No.: 13/579,065

(22) PCT Filed: Jan. 28, 2011

(86) PCT No.: PCT/CN2011/070737
§ 371 (c)(1),
(2), (4) Date: Nov. 27, 2012

(87) PCT Pub. No.: WO2011/095110
PCT Pub. Date: Aug. 11, 2011

(65) Prior Publication Data
US 2013/0066102 A1    Mar. 14, 2013

(30) Foreign Application Priority Data
Feb. 6, 2010 (CN) .......................... 2010 1 0108504

(51) Int. Cl.
C07C 271/22 (2006.01)
C07C 269/06 (2006.01)
C07C 231/02 (2006.01)

(52) U.S. Cl.
CPC .............. *C07C 231/02* (2013.01); *C07C 271/22* (2013.01); *C07C 269/06* (2013.01)
USPC .............. 560/29; 564/132; 564/143; 564/193

(58) Field of Classification Search
CPC .. C07C 231/12; C07C 231/14; C07C 237/16; C07C 269/04; C07C 269/06; C07C 271/22
USPC .............................. 560/29; 564/132, 143, 193
See application file for complete search history.

(56) References Cited

U.S. PATENT DOCUMENTS

| 6,048,899 | A | 4/2000 | Kohn et al. |
| 2008/0027137 | A1* | 1/2008 | Riedner et al. ................ 514/561 |
| 2011/0130350 | A1 | 6/2011 | Riedner |

FOREIGN PATENT DOCUMENTS

| CN | 1989102 A | 6/2007 |
| WO | 2006037574 A1 | 4/2006 |
| WO | 2009145816 A2 | 12/2009 |

OTHER PUBLICATIONS

Ma et al; Synthesis of Lacosamide; Chinese Journal of Pharmaceuticals, 40(9), Dec. 31, 2009, 641-643.
Morieux et al; The Structure-Activity Relationship of the 3-oxy Site in the Anticonvulsant (R)-N-Benzyl-2-Acetamido-3-methoxypropionamide, Journal of Medicinal Chemistry, Jul. 8, 2010, vol. 53, No. 15, pp. 5716-5726.
Morieux et al; Synthesis and anticonvulsant activities of N-Benzyl-2(R)-2-Acetamido-3-oxysubstituted propionamide deerivatives. Bioorganic & Medicinal Chemistry, Aug. 28, 2008, vol. 16, No. 19, pp. 8968-8975.
Cocinero et.al; Peptide secondary structures in the gas phase: consensus motif of N-linked glycoproteins.Journal of the American Chemical Society,2009,131(3),1282-1287.

\* cited by examiner

*Primary Examiner* — Shailendra Kumar
(74) *Attorney, Agent, or Firm* — Irving M. Fishman

(57) ABSTRACT

A new compound is provided, which is used for preparing lacosamide. A novel method for preparing lacosamide is also provided. During the reaction, iodomethane and silver oxide that are cost expensive are not used, nor a Pd-c catalyst is used, so the production cost is low, the raw materials and accessory materials are cheap and easily available, and the process is simple, so that industrial production is easy to realize; and moreover, the yield is high, and good economic efficiency can be achieved.

(I)

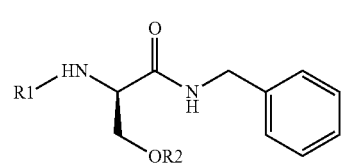

9 Claims, No Drawings

LACOSAMIDE INTERMEDIATE COMPOUND, PREPARATION METHOD THEREOF AND USE THEREOF

This application is a 35 USC 371 US National Stage filing of PCT/CN2011/070737 filed Jan. 28, 2011, which claims priority to Chinese Patent Application No. 2010101085043, filed with the Chinese Patent Office on Feb. 6, 2010 and entitled "LACOSAMIDE INTERMEDIATE COMPOUND, PREPARATION METHOD THEREOF AND USE THEREOF", which is incorporated herein by reference in its entirety.

FIELD OF THE INVENTION

The present invention relates to the field of organic chemistry and medical chemistry, in particular, to an intermediate compound of medication lacosamide, and a preparation method thereof and a use thereof.

BACKGROUND OF THE INVENTION

Lacosamide, chemical name: (R)-N-benzyl-2-acetamido-3-methoxypropionamide, CAS number: 175481-36-4, has a structural formula shown below:

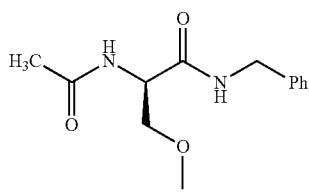 [SMILES: COC[C@@H](NC(C)=O)C(=O)NCc1ccccc1]

Lacosamide is a medication for treating epilepsy and neuropathic pain developed by Schwarz biosciences in Germany, and is used for the adjunctive treatment of partial-onset epilepsy in 16 years old or older patients with or without secondary generalized seizures. Lacosamide, also referred to as erlosamide, has an action mode different from that of all the current commercially available antiepileptic drugs: lacosamide regulates the activity of sodium channels, while other commercially available antiepileptic drugs block the sodium channels. The sodium channels play a vital role in adjustment of nervous system activity for nerve cell communication. Sometimes, abnormal hyperactivity of the sodium channel may cause seizures of epilepsy. Therefore, the action mode of lacosamide is considered as to reduce the hyperactivity of the sodium channels, and the motion of adjusting nerve cells may control the seizures of epilepsy. Clinical studies also indicate that, lacosamide is bound to collapse response mediator protein-2 (CRMP-2, mainly distributed in phosphoprotein in the nervous system for neurounal differentiation and for controlling axonal overgrowth), and lacosamide is the unique antiepileptic drug on the market that interacts with CRMP-2.

In U.S. Pat. No. 6,048,899 (patentee: Research Corporation Tech., Inc., publication date: Apr. 11, 2000), Lacosamide is first reported, and the preparation process is shown below:

Route one:

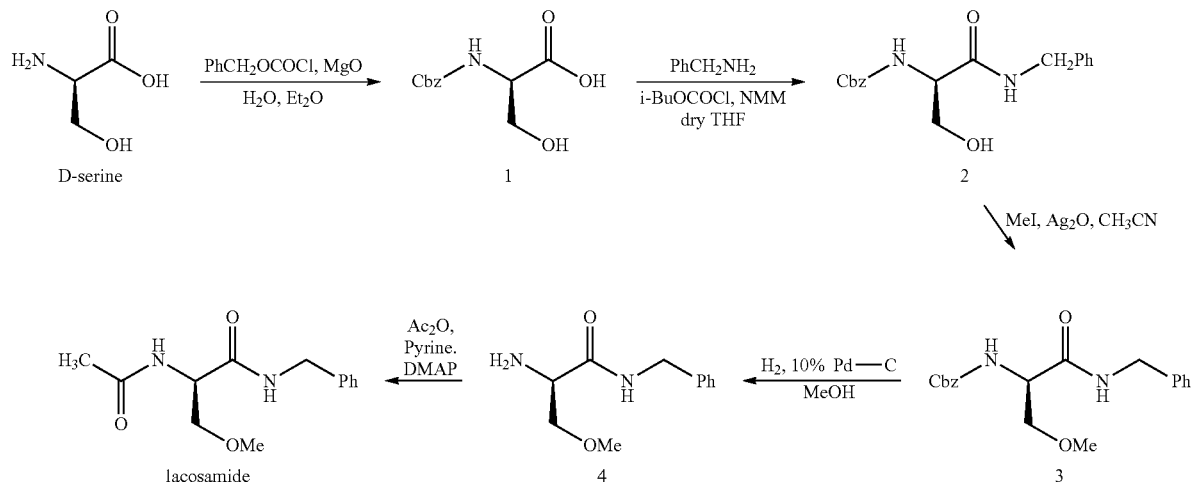

where the group -Cbz specifically is benzyloxycarbonyl, that is,

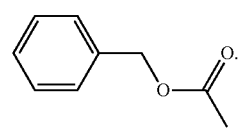

Note: the group -Cbz in the following structures and specifications are as defined above.

In this route, two critical intermediates, that is, Compound 2 and Compound 3 are involved:

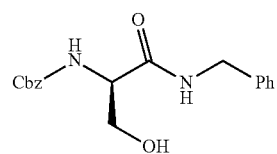

3

-continued

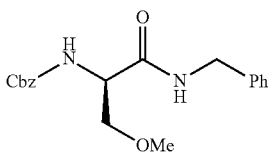

In the preparation of lacosamide through the reactions mentioned above, iodomethane and silver oxide that are cost expensive need to be used, which is not beneficial to industrial production; and moreover, in deprotection of the group Cbz, a Pd—C catalyst is used, and the production cost is high.

In U.S. Pat. No. 6,048,899, another route, that is, Route two, is disclosed:

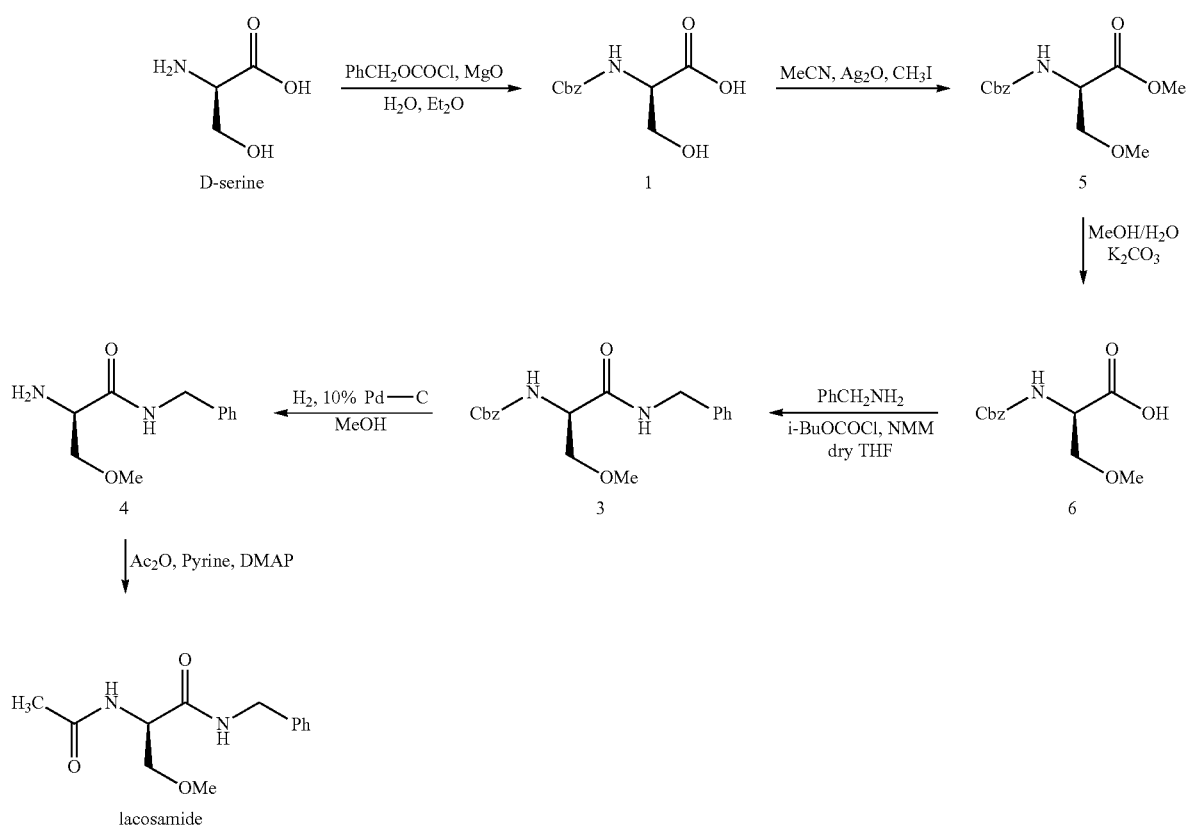

The difference between Route two and Route one lies in that, Compound 1 is subjected to an alkylation reaction; next, Compound 6 is subjected to a condensation reaction, to obtain Compound 3. It can be found through comparison with Route one that, the order of the alkylation reaction and the condensation reaction is reverse. The common features of the two routes are that: reagents and methods used in the alkylation reaction and the condensation reaction are substantially the same; during the reactions, a benzyloxycarbonyl group is used to protect the amino group, so a process of protection of the benzyloxycarbonyl group and a process of deprotection of the benzyloxycarbonyl group are involved, and the methods corresponding to the two steps are the same; and finally, the methods for preparing lacosamide from Compound 4 are the same. Therefore, it can be seen that, during the preparation of lacosamide, the order of the alkylation reaction and the condensation reaction and the step and method for protecting the amino group are very important.

DESCRIPTION OF THE INVENTION

The present invention is directed to a new compound, which is used for preparing lacosamide.

The present invention is also directed to a method for preparing the new compound.

The present invention is also directed to a novel method for preparing lacosamide.

The new compound according to the present invention has a structural formula represented by Formula (I):

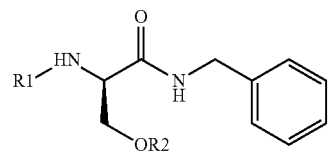

(I)

where R1 may be benzyloxycarbonyl (Cbz), 9-fluorenemethoxycarbonyl (Fomc), 2-biphenylyl-2-propoxycarbonyl (BPoc), phthalimidyl, p-tosyl, trifluoroacetyl, formyl (—HCO), acetyl (CH$_3$CO—), benzoyl (PhCO—), benzyl, allyl, dialkyl phosphoryl, tert-butoxycarbonyl (Boc), or a C$_1$-C$_{20}$ aliphatic alkoxycarbonyl; R2 may be hydrogen, hydroxyl, a C$_1$-C$_{20}$ aliphatic hydrocarbyl, or an aromatic hydrocarbyl; and when R2 is methyl, R1 is not acetyl, benzyloxycarbonyl, or tert-butoxycarbonyl; and when R2 is hydrogen, R1 is not benzyloxycarbonyl.

In a preferred compound represented by Formula (I) according to the present invention, R1 is benzyloxycarbonyl (Cbz), tert-butoxycarbonyl (Boc), or ethoxycarbonyl (CH₃CH₂O(O)C—).

A more preferred compound represented by Formula (I) according to the present invention specifically is:

(R)-N-benzyl-2-(ethoxycarbonylamino)-3-hydroxypropionamide; and (R)-N-benzyl-2-(ethoxycarbonylamino)-3-methoxypropionamide.

In the compound represented by Formula (I), when R2 is hydrogen, the structure is shown by Formula (I-1):

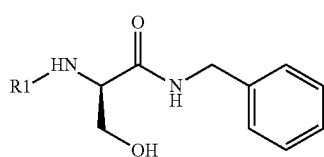

(I-1)

where R1 is 9-fluorenemethoxycarbonyl, 2-biphenylyl-2-propoxycarbonyl, phthalimidyl, p-tosyl, trifluoroacetyl, formyl, acetyl, benzoyl, benzyl, allyl, dialkyl phosphoryl, tert-butoxycarbonyl, or a $C_1$-$C_{20}$ aliphatic alkoxycarbonyl.

The compound represented by Formula (I-1) may be prepared from a compound represented by Formula (II) ((R)-2-amino-N-benzyl-3-hydroxypropionamide) and a compound represented by R1-R3, and the specific reaction is shown below:

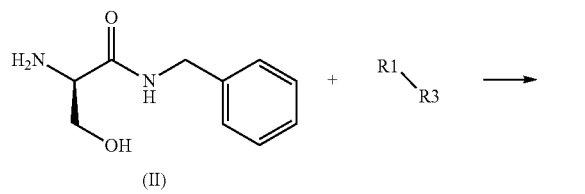

(II)

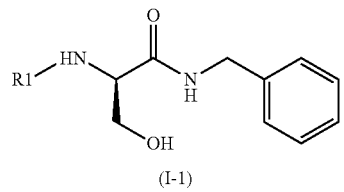

(I-1)

where R1 is defined as in the compound represented by Formula (I); and R3 may be a halogen (such as F, Cl, Br, or I), with chloride being preferred; and moreover, Compound R1-R3 is preferably ethyl chlorocarbonate; and the prepared compound represented by Formula (I-1) is preferably (R)-N-benzyl-2-(ethoxycarbonylamino)-3-hydroxypropionamide.

In the compound represented by Formula (I), when R2 is a $C_1$-$C_{20}$ aliphatic hydrocarbyl, the structural formula, is as shown in Formula (I-2):

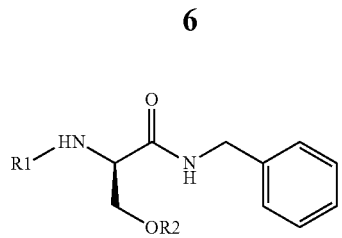

(I-2)

where R1 is benzyloxycarbonyl, 9-fluorenemethoxycarbonyl, 2-biphenylyl-2-propoxycarbonyl, phthalimidyl, p-tosyl, trifluoroacetyl, formyl, acetyl, benzoyl, benzyl, allyl, dialkyl phosphoryl, tert-butoxycarbonyl, or a $C_1$-$C_{20}$ aliphatic alkoxycarbonyl; R2 is a $C_1$-$C_{20}$ aliphatic hydrocarbyl; and when R2 is methyl, R1 is not acetyl, benzyloxycarbonyl, or tert-butoxycarbonyl.

The compound represented by Formula (I-2) may be prepared by the compound represented by Formula (I-1) through an alkylation reaction, and the specific reaction is shown below:

Method a:

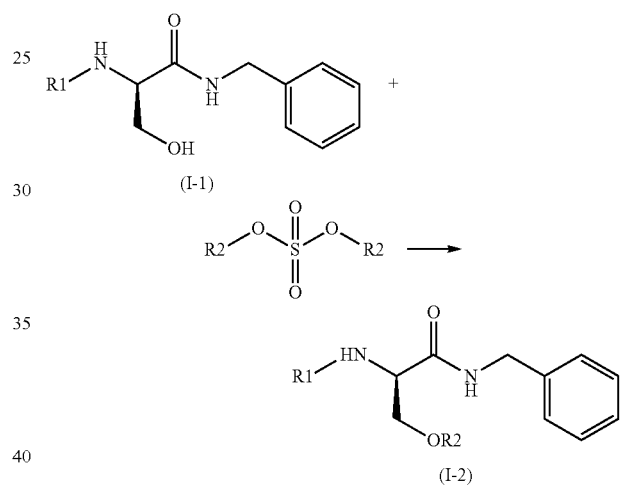

(I-1)

(I-2)

Method b:

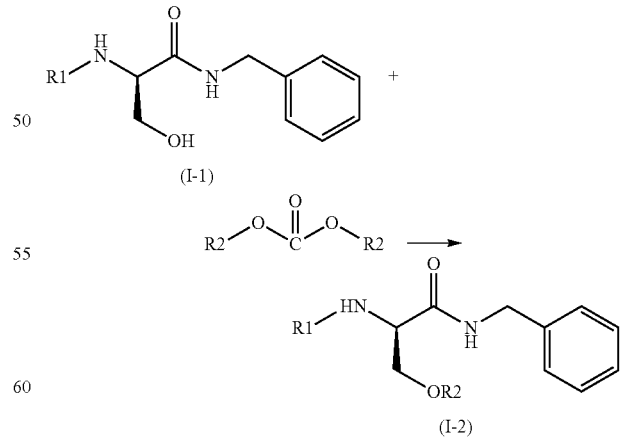

(I-1)

(I-2)

In the above two reactions. R1 is benzyloxycarbonyl, 9-fluorenemethoxycarbonyl, 2-biphenylyl-2-propoxycarbonyl, phthalimidyl, p-tosyl, trifluoroacetyl, formyl, benzoyl, benzyl, allyl, diallyl phosphoryl, tert-butoxycarbonyl, or a $C_1$-$C_{20}$ aliphatic alkoxycarbonyl; R2 is a $C_1$-$C_{20}$ aliphatic hydrocarbyl; and when R1 is benzyloxycarbonyl, acetyl, or tert-butoxycarbonyl, R2 is not methyl.

Furthermore, the alkylating agent for the alkylation reaction is preferably dimethyl sulfate; the reactant (I-1) is preferably (R)-N-benzyl-2-(ethoxycarbonylamino)-3-hydroxypropionamide; the prepared compound represented by Formula (I-2) is preferably (R)-N-benzyl-2-(ethoxycarbonylamino)-3-methoxypropionamide.

A method for preparing the compound represented by Formula (II) includes: condensating (R)-2-(tert-butoxyamino)-3-hydroxyl propionic acid (Compound (IV)) and benzylamine to obtain (R)-N-benzyl-2-(tert-butoxycarbonylamino)-3-hydroxypropionamide (Compound (III)); and deprotecting Compound (III) to obtain (R)-2-amino-N-benzyl-3-hydroxypropionamide (Compound (II)). Furthermore, the specific reaction formulas are shown below:

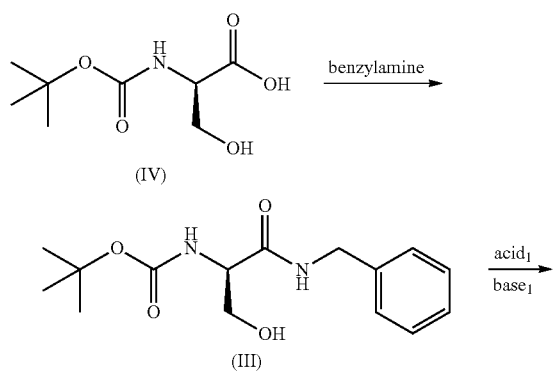

Furthermore, the acid 1 may be an inorganic acid or trifluoroacetic acid; and preferably hydrochloric acid.

Furthermore, the base 1 may be an inorganic base; and preferably sodium hydroxide or potassium hydroxide.

The compound represented by Formula (I) may be used to prepare a compound represented by Formula (V) and medication lacosamide, that is, Compound (I) is deprotected to obtain the compound represented by Formula (V); Compound (V) reacts with acetyl chloride to obtain lacosamide. Furthermore, the specific reaction formulas are shown below:

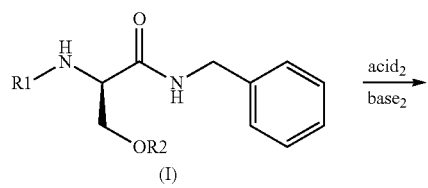

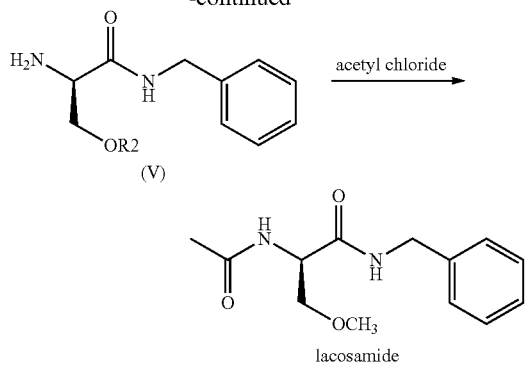

where R1 and R2 are defined as in the compound represented by Formula (I); and R1 is preferably ethoxycarbonyl, and R2 is preferably methyl.

Furthermore, the acid 2 may be an inorganic acid or trifluoroacetic acid; and preferably hydrochloric acid.

Furthermore, the base 2 may be an inorganic base; and preferably sodium hydroxide or potassium hydroxide.

The present invention has the following beneficial effects. A new compound is provided, which can be used to prepare lacosamide; and a novel method for preparing lacosamide is also provided. During the reactions, iodomethane and silver oxide that are cost expensive are not used, nor a Pd—C catalyst is used, so the production cost is low, the raw materials and accessory materials are cheap and easily available, and the process is simple, so that industrial production is easy to realize; and moreover, the yield is high, and good economic efficiency can be achieved.

EMBODIMENTS

Hereinafter, the present invention is described with reference to the following embodiments.

Embodiment 1

Preparation of (R)-N-benzyl-2-(tert-butoxycarbonylamino-3-hydroxypropionamide

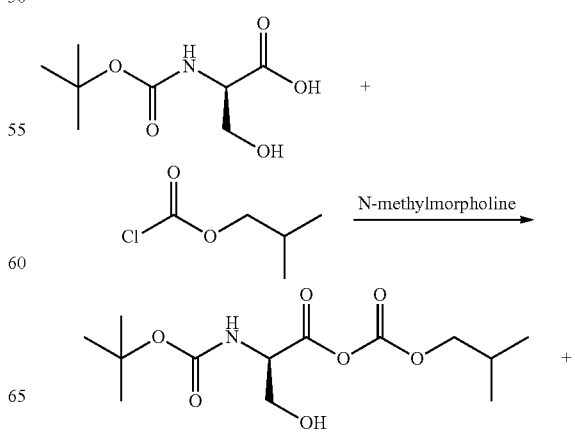

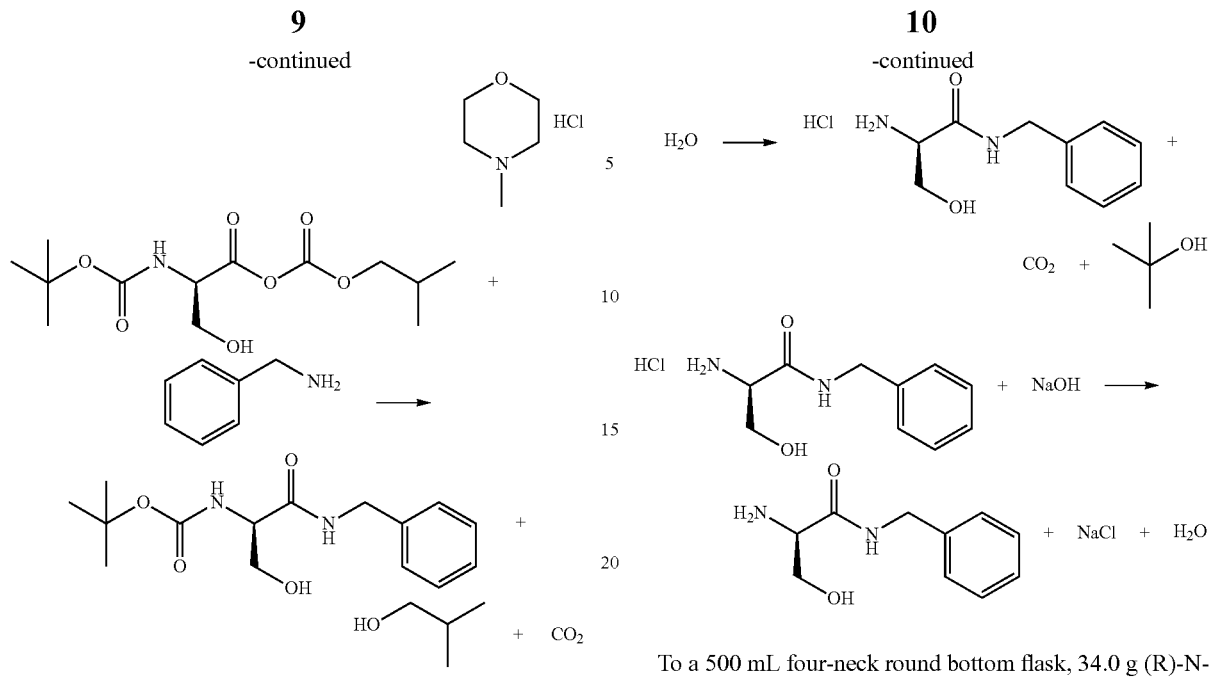

32.16 g (0.30 mol) benzyl amine was dissolved in 150 g anhydrous ethyl acetate to formulate a solution for use.

To a 1000 mL four-neck round bottom flask, 51.5 g (0.25 mol) (R)-2-(tert-butoxyamino)-3-hydroxypropionic acid and 450 g anhydrous ethyl acetate were added in sequence, and mechanical stirring was started. The temperature was decreased to −10° C. 27.83 g (0.275 mol) N-methylmorpholine and 37.59 g (0.275 mol) isobutyl chloroformate were added into the system. After addition, the formulated benzyl amine-ethyl acetate solution (32.16 g benzyl amine dissolved in 150 g anhydrous ethyl acetate) was added at −15 to −10° C. Then, the temperature was raised to 10-15° C., and reaction was performed at this temperature. After reaction, 200 g tap water was added, and the mixture was stirred for several minutes, and stood for layering. An organic layer was separated, and washed with 200 g dilute hydrochloric acid and 200 g saturated aqueous solution of sodium chloride. The solvent was evaporated, to obtain a colorless transparent oily substance, which was triturated with petroleum ether and suction-filtered. A filter cake was leached with a suitable amount of petroleum ether, and then dried in an oven. Finally, 53.0 g (0.180 mol) target product was obtained. The molar yield was 71.86%, and the HPLC purity was 94.84%. The product can be directly used in a following reaction without further purification.

Embodiment 2

Preparation of (R)-2-amino-N-benzyl-3-hydroxypropionamide

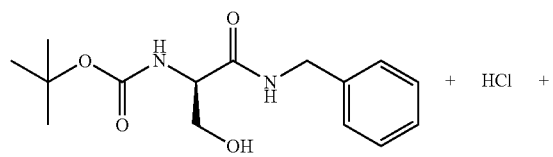

To a 500 mL four-neck round bottom flask, 34.0 g (R)-N-benzyl-2-(tert-butoxycarbonylamino)-3-hydroxypropionamide and 350 mL dichloromethane were added, and the mixture was stirred to obtain a clear solution. At 20-25° C., 40.0 g concentrated hydrochloric acid (having a mass concentration of 36.0%) was added, and the reaction was continued. TLC tracking was performed, till the raw materials were completely converted. After the reaction was completed, the temperature was decreased to 20° C. The mixture was suction-filtered, to obtain a white needle-like crystal. The obtained white crystalline solid was dissolved in 50 g water. At 20-25° C., 30% sodium hydroxide solution was added to adjust the pH value of the system to 8-9. After the addition, the solution was stirred continuously, and a white flaky crystal was precipitated. The mixture was suction-filtered, and the filter was washed and dried, to obtain a target product of 16.5 g (0.085 mol). The molar yield was 73.52%.

Embodiment 3

Preparation of (R)-N-benzyl-2-(ethoxycarbonylamino)-3-hydroxypropionamide

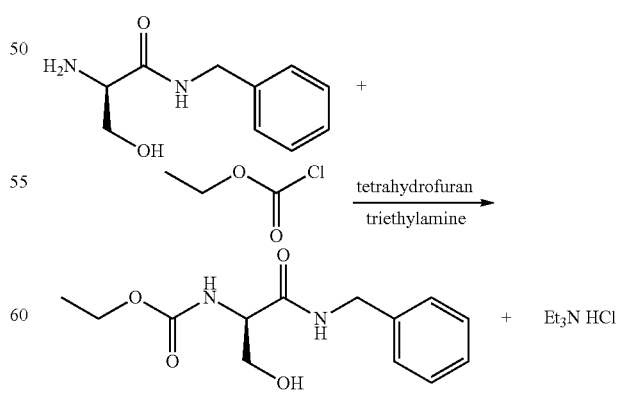

To a 250 mL three-neck round bottom flask, 9.65 g (0.0497 mol) (R)-2-amino-N-benzyl-3-hydroxypropionamide, 120 mL tetrahydrofuran, and 7.58 g (0.0749 mol) triethylamine were added in sequence, the mixture was stirred to obtain a solution. At a normal temperature, 6.01 g (0.0554 mol) ethyl chlorocarbonate was added. After the reaction was completed, the solvent was evaporated, and the residue was added with 100 mL water, and stirred uniformly. The solution was extracted with 50 mL×3 ethyl acetate, and the organic phases were combined and dried over anhydrous sodium sulfate. The solvent was evaporated, to obtain a white solid of 9.67 g (0.0363 mol). The molar yield was 73.04%.

Embodiment 4

Preparation of (R)-N-benzyl-2-(ethoxycarbonylamino)-3-methoxypropionamide

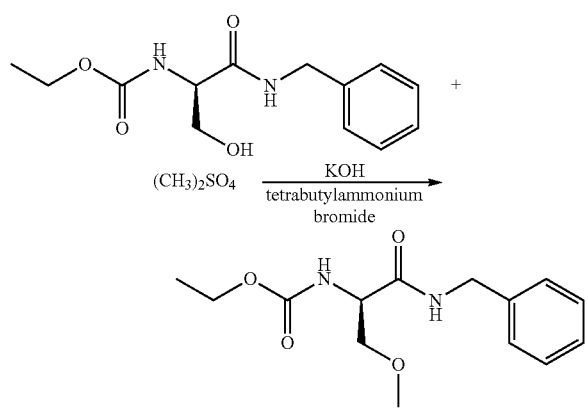

To a 500 mL three-neck round bottom flask, 7.2 g (0.027 mol) (R)-N-benzyl-2-(ethoxycarbonylamino)-3-hydroxypropionamide, 300 mL ethyl acetate, 27.2 g (0.216 mol) dimethyl sulfate, and 2.0 g tetrabutylammonium bromide were added in sequence. At a normal temperature, 24.8 g 50% potassium hydroxide (0.2214 mol) solution was added. After the reaction was completed, 100 mL water was added, and the mixture was stirred for several minutes, and stood for layering. An organic layer was separated, and washed with a saturated sodium chloride aqueous solution and dried over anhydrous sodium sulfate. The solvent was evaporated, to obtain a transparent oily substance, which was triturated with n-hexane, suction-filtered, washed, and dried, to obtain a white solid of 5.37 g (0.01916 mol). The molar yield was 70.96%.

Embodiment 5

Preparation of (R)-2-amino-N-benzyl-3-methoxypropionamide

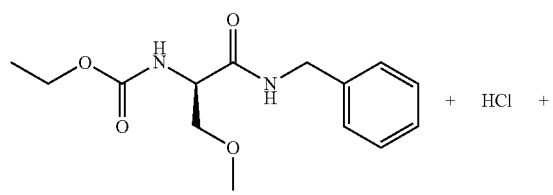

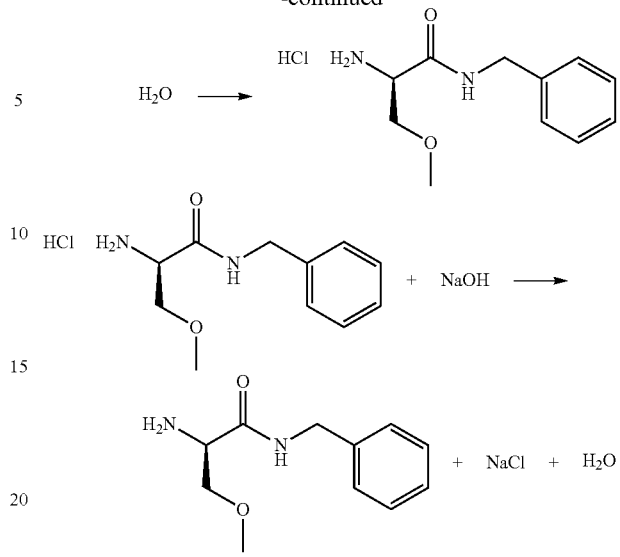

To a 100 mL single-neck flask, 5.6 g (0.02 mol) (R)-N-benzyl-2-(ethoxycarbonylamino)-3-methoxypropionamide and 50 mL 31% concentrated hydrochloric acid were added, the mixture was heated and refluxed for 6-10 hr. After the reaction was completed, 30% sodium hydroxide solution was added to adjust the pH value of the system to 8-9. The reaction liquid was extracted with 50 mL×2 dichloromethane, and dried over anhydrous sodium sulfate. The product can be directly used in following synthesis without further purification.

Embodiment 6

Preparation of (R)-2-acetylamino-N-benzyl-3-methoxypropionamide

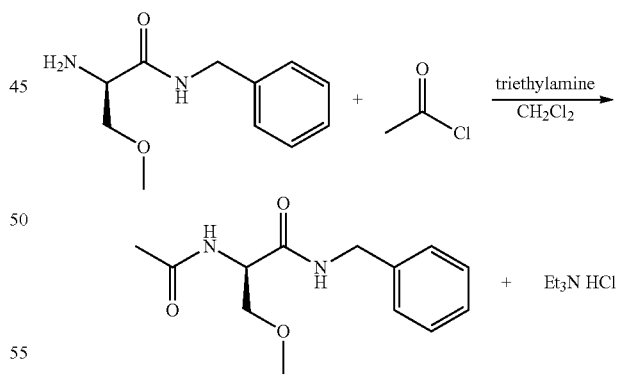

To a 100 mL three-neck round bottom flask, the organic obtained in Embodiment 5 and 2.22 g (0.022 mol) triethylamine were added, and the temperature was decreased to 10° C. At 10-25° C., 1.73 g (0.022 mol) acetyl chloride was added slowly. After addition, the reaction was continued, till the raw materials were completely converted. After the reaction was completed, the reaction liquid was washed with 40 g×2 saturated sodium bicarbonate solution. The solvent as evaporated, to obtain 3.92 g white solid. The product was recrystallized with an n-hexane-ethyl acetate mixture solvent, to obtain a white powder solid of 3.12 g (0.0125 mol). The molar yield was 62.4% (with respect to (R)-N-benzyl-2-(ethoxycarbonylamino)-3-methoxypropionamide).

The above description is merely preferred embodiments of the present invention. It should be noted that, persons of ordinary skill in the art can make several improvements and modifications without departing from the principle of the present invention, and the improvements and modifications should also be construed as falling within the protection scope of the present invention.

What is claimed is:

1. A method for preparing the compound of formula (I-1),

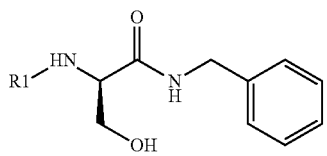
(I-1)

comprising using a compound represented by Formula (II) and a compound represented by R1-R3:

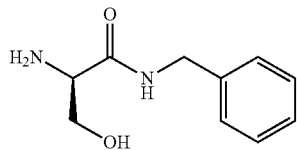
(II)

wherein R1 is 9-fluorenemethoxycarbonyl, 2-biphenylyl-2-propoxycarbonyl, phthalimidyl, p-tosyl, trifluoroacetyl, formyl, acetyl, benzoyl, benzyl, allyl, dialkyl phosphoryl, tert-butoxycarbonyl, or a $C_1$-$C_{20}$ aliphatic alkoxycarbonyl; and R3 is a halogen.

2. The method according to claim 1, further comprising a step of an alkylation reaction of the compound represented by Formula (I-1) and

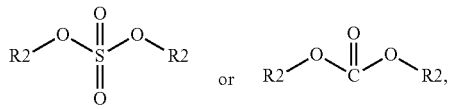

to afford a compound of formula (I-2),

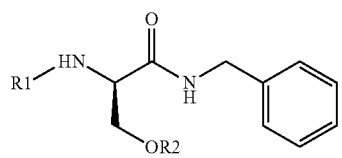
(I-2)

wherein R1 is 9 fluorenemethoxycarbonyl, 2-biphenylyl-2-propoxycarbonyl, phthalimidyl, p-tosyl, trifluoroacetyl, formyl, acetyl, benzoyl, benzyl, allyl, dialkyl phosphoryl, tert-butoxycarbonyl, or a $C_1$-$C_{20}$ aliphatic alkoxycarbonyl; R2 is a $C_1$-$C_{20}$ aliphatic hydrocarbyl.

3. The preparation method according to claim 2, wherein an alkylating agent for the alkylation reaction is dimethyl sulfate.

4. A method for preparing lacosamide, comprising:
Step 1: preparing the compound represented by Formula (I-2) according to the method as defined in claim 2 and deprotecting the compound of Formula (I-2), to obtain a compound represented by Formula (V):

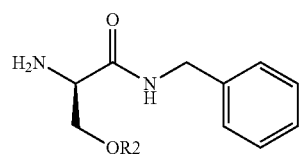
(V)

wherein R1 and R2 are as defined in claim 2;
Step 2: reacting the compound of Formula (V) with acetyl chloride, to prepare lacosamide.

5. The preparation method according to claim 4, wherein the deprotection reaction is performed in the presence of trifluoroacetic acid or an inorganic acid or an inorganic base.

6. The method for preparing (R)-2-amino-N-benzyl-3-hydroxypropionamide according to claim 1, comprising:
condensating (R)-2-(tert-butoxyamino)-3-hydroxylpropionic acid and benzylamine to obtain (R)-N-benzyl-2-(tert-butoxycarbonylamino)-3-hydroxypropionamide, and
deprotecting (R)-N-benzyl-2-(tert-butoxycarbonylamino)-3-hydroxypropionamide to obtain (R)-2-amino-N-benzyl-3-hydroxypropionamide.

7. The preparation method according to claim 6, wherein the deprotection reaction is performed in the presence of trifluoroacetic acid or an inorganic acid or an inorganic base.

8. The method of claim 5 wherein said inorganic acid is hydrochloric acid and said inorganic base is selected from sodium hydroxide and potassium hydroxide.

9. Then method of claim 7 wherein said inorganic acid is hydrochloric acid and said inorganic base is selected from sodium hydroxide and potassium hydroxide.

* * * * *